United States Patent
Bengtsson

[11] Patent Number: 6,078,390
[45] Date of Patent: Jun. 20, 2000

[54] SCANNING SYSTEM AND METHOD OF OPERATION FOR AUTOMATICALLY SETTING DETECTION SENSITIVITY

[75] Inventor: Hans Bengtsson, Sudbury, Mass.

[73] Assignee: General Scanning, Inc., Watertown, Mass.

[21] Appl. No.: 09/071,982

[22] Filed: May 4, 1998

[51] Int. Cl.[7] .................................................. G01N 21/64
[52] U.S. Cl. .................. 356/318; 250/252.1; 250/458.1; 356/417
[58] Field of Search ..................................... 356/317, 318, 356/417; 250/252.1 A, 458.1, 459.1, 461.1, 461.2

[56] References Cited

U.S. PATENT DOCUMENTS

| | | |
|---|---|---|
| 4,482,252 | 11/1984 | Lorenz . |
| 4,489,236 | 12/1984 | Outhwaite . |
| 4,758,727 | 7/1988 | Tomei et al. . |
| 4,833,332 | 5/1989 | Robertson, Jr. et al. . |
| 4,877,966 | 10/1989 | Tomei et al. . |
| 5,053,626 | 10/1991 | Tillotson . |
| 5,194,916 | 3/1993 | Hayashi . |
| 5,212,538 | 5/1993 | Hayashi . |
| 5,239,171 | 8/1993 | Takabayashi et al. . |
| 5,296,703 | 3/1994 | Tsien . |
| 5,302,824 | 4/1994 | Prager . |
| 5,426,306 | 6/1995 | Kolber et al. . |
| 5,437,840 | 8/1995 | King et al. . |
| 5,459,325 | 10/1995 | Hueton et al. . |
| 5,538,850 | 7/1996 | King et al. . |
| 5,600,147 | 2/1997 | Jensen . |
| 5,631,734 | 5/1997 | Stern et al. . |
| 5,633,724 | 5/1997 | King et al. . |
| 5,646,411 | 7/1997 | Kain et al. . |
| 5,672,880 | 9/1997 | Kain . |
| 5,689,110 | 11/1997 | Dietz et al. . |

OTHER PUBLICATIONS

ScanArray 3000 Biochip Scanning System Instruction Manual, General Scanning Inc. Optical Scanning Products Division, Feb. 3, 1998.

*Primary Examiner*—F. L. Evans
*Attorney, Agent, or Firm*—Cesari and McKenna, LLP

[57] ABSTRACT

An optical scanning system uses a low-resolution scanning operation, to automatically adjust the sensitivity of the system. The system performs a low-resolution scanning operation by scanning a line, automatically and iteratively setting the levels of excitation signal power and detector gain, skipping a plurality of lines and scanning a next line, adjusting the levels as appropriate, skipping a plurality of lines and scanning a next line, and so forth. After the system sensitivities have been set, the calibrated system then scans all the lines of the sample to collect data. The calibrated system thus scans for the first time the lines that were skipped during the low resolution scanning operation.

35 Claims, 5 Drawing Sheets

SCANNING SYSTEM AND METHOD OF OPERATION FOR AUTOMATICALLY SETTING DETECTION SENSITIVITY

FIELD OF THE INVENTION

This invention relates to optical scanners and, more particularly, to mechanisms for setting the detection sensitivity of optical scanners.

BACKGROUND OF THE INVENTION

One use for optical scanners is to detect fluorescence that is emitted from a sample that has been excited by a laser excitation signal. The sample may consist of a "micro-array" of elements, typically in the shape of dots, that contain chemicals, DNA and so forth that are under study. The dots, which have diameters that are measured in microns, include fluorescent tags that emit fluorescent light in response to excitation by the laser. The amount of fluorescence emitted by a dot indicates, for example, the results of a particular chemical reaction that has taken place.

Generally, a user has little idea of the brightness of the fluorescence that will be emitted by a particular sample. Accordingly, the user does not know apriori how high or low to set the attenuation of an attenuator that controls the optical excitation signal power, that is, the signal power that reaches the sample. Further, the user does not know how high or low to set the gain of a detector that collects the emitted fluorescence and produces a corresponding data signal. If the excitation signal power and/or detector gain are set too high, the system saturates, and thus, fails to make accurate measurements. If the excitation power and/or gain are set too low, the system may not accurately distinguish between different lower levels of emitted fluorescence.

In certain known prior systems, the sensitivity of the system is set by the user, who manually adjusts both the gain of the fluorescence detector and the level of attenuation of the attenuator. Typically, the user scans the sample in raster fashion, to locate an element in the micro-array that is known to contain a concentration of a fluorophor that should produce a maximum fluorescence in response to the excitation signal. The user then re-scans the portion of the sample that contains this element and iteratively adjusts the sensitivity of the system until, in the judgment of the user, the corresponding data signal is sufficiently close to a maximum data signal value of the system. If the system has two channels, that is, produces excitation signals using two lasers of different wavelengths, the user re-scans the sample using as the excitation signal the signal produced by the second laser and repeats the iterative, manual adjustment process to determine the appropriate sensitivity settings for the second channel. Similarly, the user further re-scans the sample for each additional channel.

The adjustment ranges of the attenuator and the detector are relatively large. Accordingly, manual adjustment of these components is time consuming, particularly since adjustment of either one of them may require a re-adjustment of the other. The sample may thus be scanned many times to set the sensitivity of, or calibrate, the system. When multiple channels are used, more time is spent manually calibrating the system and the sample is scanned even more times, as discussed above.

The scanning and re-scanning of the sample may damage the sample. For instance, repeated exposure to the laser signal power may cause "photo-bleaching," which results in a weakening of the fluorescence emitted in response to subsequent excitation. This means that the data collection operations may be adversely affected, particularly with respect to sample elements that produce low levels of fluorescence. The risk of damage to the sample is further increased when multiple channels are used.

SUMMARY OF THE INVENTION

The inventive system uses a low-resolution scanning operation, to automatically adjust the sensitivity of the system. The system performs a low-resolution scanning operation by scanning a line, automatically and iteratively setting the levels of optical signal power and detector gain, skipping a plurality of lines and scanning a next line, adjusting the levels as appropriate, skipping a plurality of lines and scanning a next line, and so forth. After the system sensitivities have been set, the calibrated system then scans all the lines of the sample to collect data. The calibrated system thus scans for the first time the lines that were skipped during the low resolution scanning operation. Accordingly, there is no risk of photo-bleaching or otherwise damaging of these skipped lines, and accurate data can be collected from them.

The system first sets the detector gain to maximum and the excitation signal power to a predetermined default value, such as half-power, and scans a first scan line of a selected area of the sample. The system then determines if the signals associated with "N" adjacent pixels in the scan line are saturated, that is, if the signals that correspond to N adjacent pixels are above a maximum data signal value. If so, the system reduces the laser excitation signal power by a predetermined factor, for example, by a factor of two. The system next re-scans the line and determines if N adjacent pixels are still saturated. If so, the system again reduces the excitation signal power by the predetermined factor. The system continues to re-scan the line until either fewer than N adjacent pixels produce saturated signals, or the excitation signal power has been reduced to a predetermined minimum power level, for example, to one-quarter of the maximum power.

If N adjacent pixels still produce saturated signals when the excitation signal power is reduced to the minimum level, the system reduces the gain of the detector by a predetermined factor, such as, by a factor of eight, and at the same time increases the excitation signal power by a predetermined factor, such as, by a factor of four. The system then re-scans the line, making the necessary adjustments to the excitation signal power, until either fewer than N adjacent pixels produce saturated signals, and/or the detector gain must be further reduced. As necessary, the gain is adjusted and the power level increased and the system continues to scan the same line and make adjustments until the levels are set for this line. The system then skips the next L lines and scans the $L+1^{st}$ line. It next adjusts the attenuation and gain levels, as appropriate, until fewer than N adjacent pixels in the line produce saturated signals. The system then skips the next L lines and scans the $L+1^{st}$ line, and so forth, until a last scan line of the selected area of the sample has been scanned. The number, L, of lines skipped is selected such that (a) there are multiple scans performed per sample dot, and (b) most of the dot remains untouched by the laser excitation signal.

After the low-resolution scan operation is completed, the system determines the average value of the signals produced by the M brightest adjacent pixels. The system then calculates the level of laser excitation signal power that is required to bring the average value to 90% of the maximum data signal value. It next adjusts the attenuator to produce at the sample an excitation signal with the calculated power. If the attenuation level can not be adjusted to bring the average value to 90% of the maximum value, the system indicates to the user that the sample is dim. Otherwise, the system uses the adjusted attenuation level for the channel.

If more than one channel is to be used, the system repeats the low-resolution scanning operation, using the signal from a next laser for the excitation signal. The system thus re-scans the first scan line, adjusts the levels, skips L lines and re-scans the L+1$^{st}$ line and so forth.

The low resolution scanning operation works well with a sample, such as micro-array, in which the fluorescence produced by an element (e.g., a dot) is essentially uniform over the element.

DETAILED DESCRIPTION OF ILLUSTRATIVE EMBODIMENTS

Figure 1:
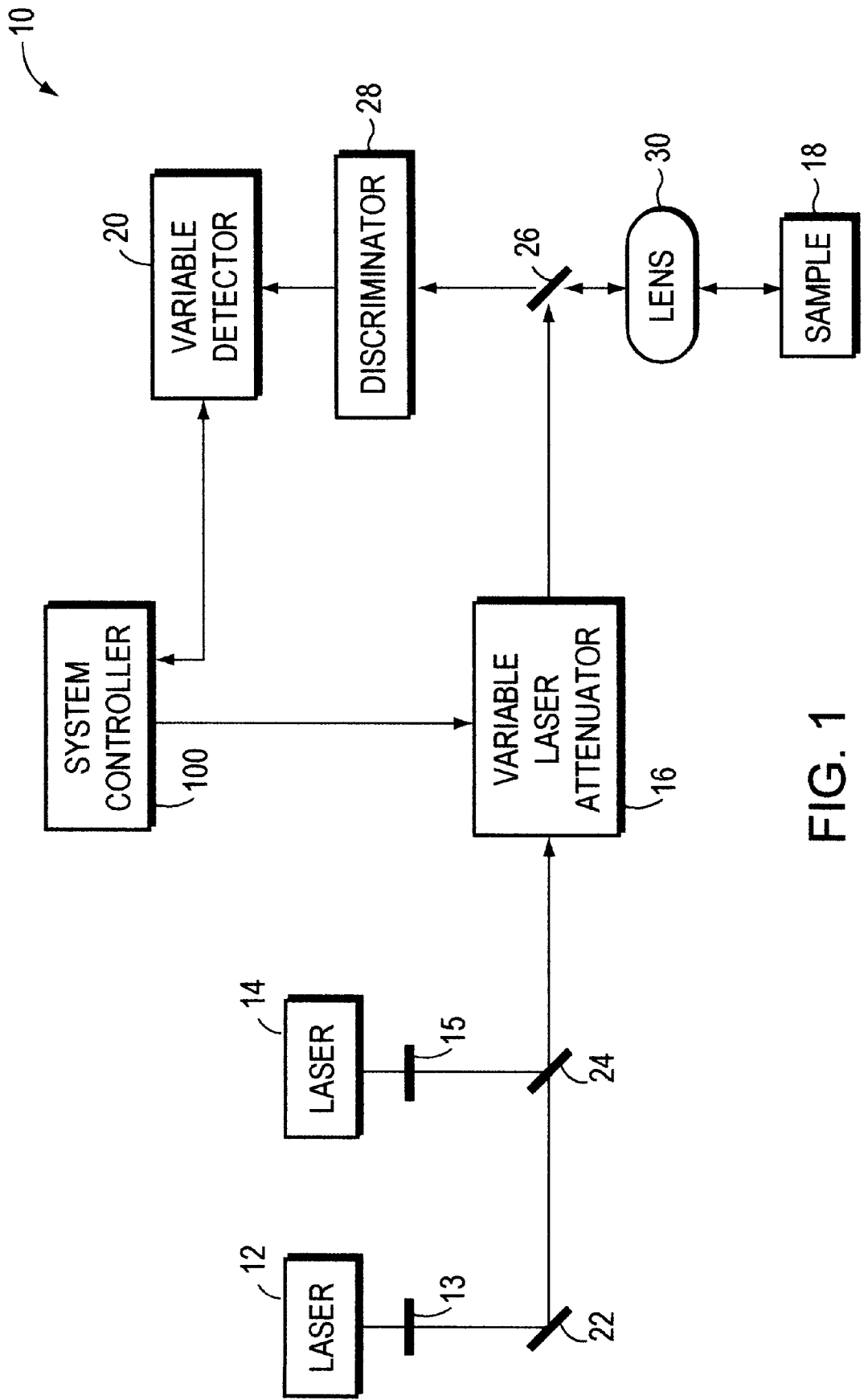
FIG. 1 is a functional block diagram of a system constructed in accordance with he invention.

FIG. 1 depicts an optical scanning system 10 that includes two lasers 12 and 14, a variable laser attenuator 16 that controls the excitation signal power that is delivered to a sample 18, and a variable gain detector 20 that receives fluorescence emitted from the sample and produces associated data signals. As discussed in more detail below, a system controller 100 controls the attenuator 16 and the detector 20, to set the sensitivity of the system appropriately for a given sample. Scanning operations that use, for example, the excitation signal produced by the laser 12 are over a first "channel," and scanning operations that use the excitation signal produced by the laser 14 are over a second channel. The term channel refers essentially to the system configured appropriately for the particular excitation signal, such as, for example, the selection of or conditioning of filters to pass or reject signals of the appropriate wavelengths and, as discussed in more detail below, the settings of appropriate levels of detector gain and attenuation levels. The drawing depicts two lasers, however, a single laser or a greater number of lasers may be included in the system with scanning operations over a corresponding number of channels, as appropriate for a particular application. Further, alternative excitation signal sources, such as, for example, xenon lamps or light-emitting-diodes, may be used instead of the lasers.

Figure 4:
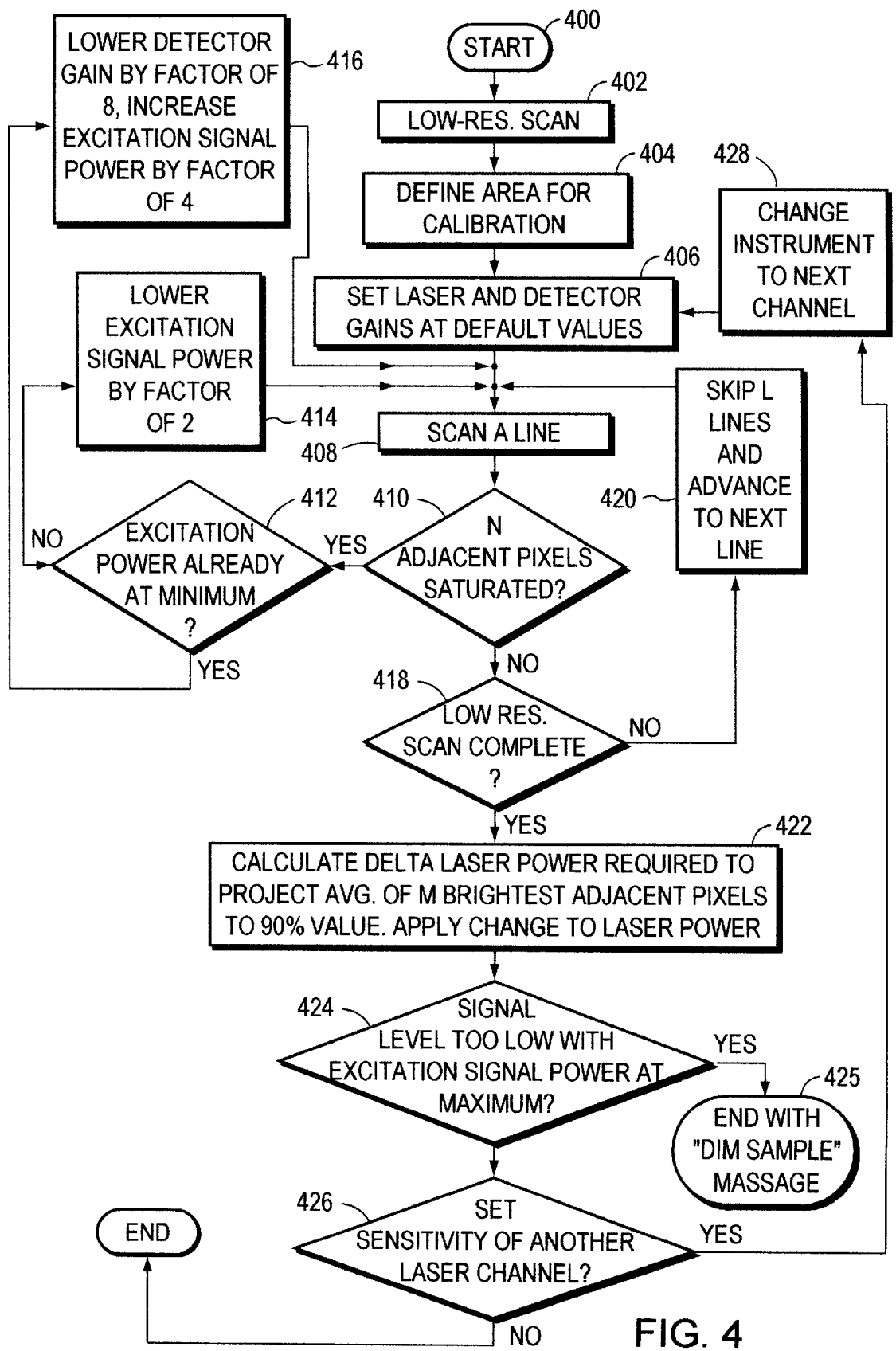
FIG. 4 is a flow chart of the operations of the system of FIG. 1 to set the levels of attenuation and detector gain.

The variable laser attenuator 16 may be, for example, an addressable array of selected neutral fixed-density filters; a continuously variable neutral density filter; a plurality of polarizers that includes at least one rotatable polarizer; or a rotating polarization retarder placed in front of a polarizer, all of which are known in the art. Alternatively, the power of the excitation signal may be varied by controlling the operations of the excitation signal source. The system controller 100 may thus control the voltage or amplitude of a signal the controls the operations of the excitation signal source. The calibration operations discussed herein with reference to FIG. 4 refer to determining for each channel the appropriate level of attenuation, to control the excitation signal power that reaches the sample. The same operations may be used instead to determine, for example, the appropriate voltage or amplitude of the signal that controls the operation of the excitation signal source, and thus, controls the power of the excitation signal produced by the source.

A mirror 22 directs the beam from the laser 12 to a beam combiner 24, which transmits light at the wavelength produced by the laser 12 and reflects light at the wavelength produced by the laser 14. The beam combiner 24 may be, for example, a dichroic filter with thin-film interference coatings that transmit and reflect light at the respective wavelengths. The beam combiner 24 may be used to combines the beams from the two lasers into a single, collimated beam. In the system 10 shutters 13 and 15 operate in a conventional manner to control the passing of light from the lasers to the beam combiner, such that at any given time light from only one laser reaches the beam combiner. The beam combiner 24 then passes or reflects the beam, as appropriate. The beam combiner thus ensures that the beams from each of the lasers travel along the same path to the sample 18.

The beam next passes through the attenuator 16, which produces an attenuated, collimated beam with a desired power level. The positions of the attenuator 16 and the beam combiner 24 may be reversed, with the beam combiner passing, reflecting or combining the attenuated beams.

A beam splitter 26 reflects the beam through a lens assembly 30. The lens assembly focuses the beam and directs it to the sample 18. The beam splitter 26 also transmits to the variable gain detector 20 the light that the lens assembly 30 collects from the sample 18.

The lens assembly 30, which is similar to a conventional microscope objective lens assembly, includes multiple elements (not shown) that are mounted in a metal cell 32. Preferably, the lens assembly has a large working distance, a limited chromatic correction range and includes an objective lens with a high numerical aperture—in the range of 0.5 to 0.8. In the system depicted in the drawing, the lens assembly consists of six elements, has a 10 mm aperture, a working distance of 0.8 mm, provides chromatic correction for laser and fluorescence wavelengths over the range of 488 nm to 690 nm, and includes an objective lens that has a numerical aperture of 0.75 and a focal length of 6.67 mm.

The lens assembly 30 focuses the combined, collimated beam that it receives from the beam splitter 28 to a spot that for a micro-array scanner is preferably within the range of approximately 1 to 20 microns in diameter measured at the full-width half-maximum point. In the system depicted in the drawing, the lens assembly produces a focused laser spot 300 (FIG. 3) that is 8 microns in diameter. The lens assembly may produce laser spots with various other diameters, as appropriate for specific applications. For example, the lens assembly may produce a laser spot with a larger diameter when the sample includes relatively large targets, or dots.

In response to the laser spot, fluorescent chemical tags in the sample emit fluorescent light that is typically at a longer wavelength than the laser light. The lens assembly 30 collects a portion of the emitted fluorescent light. More specifically, it collects the fluorescent light that is emitted within an area that represents a solid angle cone that corresponds to the numerical aperture of the objective lens. Accordingly, the higher the numerical aperture of the objective lens, the more light the lens assembly collects.

The lens assembly 30 collimates and focuses the collected fluorescent light and directs it to a fluorescence emission wavelength discriminator 28. The discriminator 28 operates in a conventional manner to filter the light from the sample. The discriminator, at any given time, passes light at a desired peak fluorescence wavelength and rejects light at other wavelengths, including light from the lasers 12 and 14 that may be reflected from the sample 18. The discriminator may be, for example, an arrangement of emission filters that pass a desired narrow spectrum of fluorescent light. Alternatively, the discriminator may be a prism or grating that likewise passes the narrow spectrum of fluorescent light.

The discriminator 28 passes the fluorescent light to the variable gain detector 20, which may be, for example, a photomultiplier tube detector, a PIN diode, a charge-coupled-device, and so forth. The detector 20 sends data signals relating to the fluorescent light to the system controller 100, which records them for later use. The operations of the system controller are discussed in more detail below with reference to FIGS. 3 and 4.

The system may include a plurality of discriminators 28 in the path of the collimated fluorescent light, and a plurality of detectors 20. Each discriminator directs fluorescent light of a desired wavelength to an associated detector 20, and rejects all other wavelengths. The detectors 20 can then be matched specifically to particular wavelengths, and scanning operations involving multiple wavelengths can be performed simultaneously. The shutters 13 and 15 thus need not be included in the system, or may be operated in synchronism to pass the multiple wavelengths.

Figure 2:
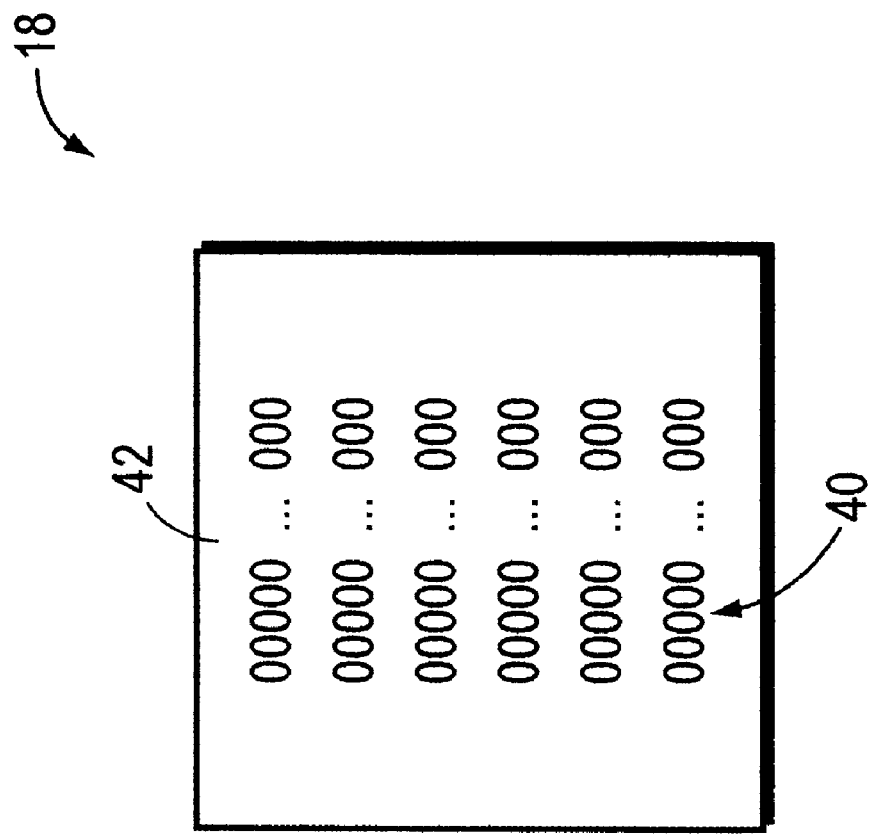
FIG. 2 is an illustration of a micro-array.

Referring now to FIG. 2, the area of the sample 18 from which data is collected (i.e., the "image") consists of a plurality of elements, or dots, 40 that are arranged in what is commonly referred to as a micro-array 42. The dots 40 in the micro-array 42 have essentially uniform diameters, which are generally in a range of between 50 and 250 microns. In the example discussed herein the dots have diameters of 150 microns. The image is dimensioned in "pixels," which in the example are 10 micron-by-10 micron squares. In the example, each scan line is approximately one pixel wide, and in the example there are 15 scan lines per dot. The scan lines may be wider or narrower than a pixel, as appropriate for a particular application.

Figure 3:
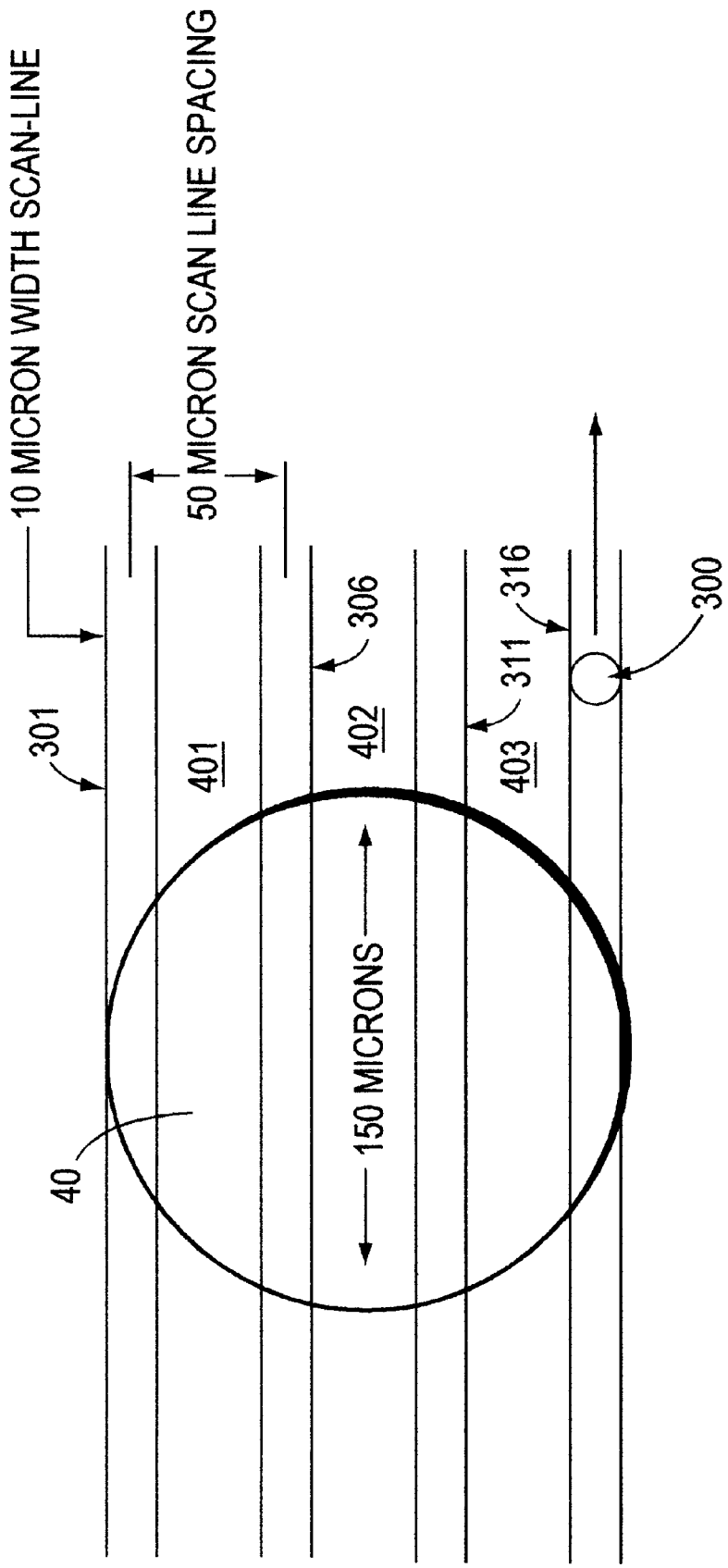
FIG. 3 is an illustration of an element in the micro-array of FIG. 2 with low-resolution scan lines indicated.

Referring now to FIG. 3, the system 10 sets the levels of attenuation and detector gain for a given sample by performing a low-resolution scanning operation. As discussed in more detail below, the system scans a scan line 301 and automatically adjusts the levels to avoid saturation, re-scanning the scan line 301 as necessary to automatically readjust one or both of the levels. The system then skips a selected number, L, of lines, four in the drawing, and scans a next, L+1$^{st}$, scan line 306. It then automatically readjusts the levels as necessary. The system again skips the next four lines and scans a fifth scan line 311, and so forth. At the end of the low resolution scan operation, the system has scanned only a small percentage of the dot 40. In the example, the system scans four 10 micron-wide lines 301, 306, 311 and 316 across a 150 micron diameter dot, and leaves three 40 micron-wide strips 401, 402, 403 of the dot untouched. Once the sensitivity of the system is set, the system can then perform a high-resolution scanning operation in which all of the lines are scanned, in order to collect the data from the sample. Most of the data collection scans are thus performed over previously untouched areas of the sample.

The low-resolution scanning operation may be used with various shapes and sizes of micro-array elements. The number of lines skipped between scans is selected such that the scan line spacing is at least twice the scan line width, and the spacing is less that one-half of the diameter of the element.

Referring now to FIGS. 1–4, the system 10 automatically sets its sensitivity for a new sample 18 by first, as necessary, locating the micro-array 42 on the sample. To locate the micro-array, the system performs a low-resolution scanning operation with one of the lasers 12 or 14 over the entire sample. This first low-resolution scan operation also provides information from which the user can choose a calibration area (step 402). The system performs this first low resolution scanning operation using a first set of default settings for attenuation and detector gain. In the example, the attenuation level is set to one-half and the detector gain is set to maximum. However, essentially any settings will work.

The system displays the results of this scanning operation on a screen (not shown) as, for example, a chart that essentially depicts the micro-array fluorescent intensity mapped as a gray scale or as "false colors." The operation does not generally produce sufficient information to define the shapes or locations of the elements within the array. Indeed, this scanning operation may produce saturated signals and/or signals that are too low to distinguish between the lower levels of fluorescence.

Once the position of the micro-array 42 is determined, the user selects a calibration area, which may be the entire micro-array or some portion of the array (step 404). The user preferably selects a portion of the micro-array for which the system produces either saturated signals or signals that indicate the brightest dots. The area may be selected by drawing a box around the area on the screen.

For some applications the user may be interested solely in the lower levels of fluorescence. Accordingly, the user may select the calibration area from a section of the micro-array that includes the dimmest dots. Calibrating over this dim region means that the signals produced for the brighter regions of the array may be saturated. However, for these applications the signals produced by the brighter dots are of essentially no interest.

The array-locating scan operation may be omitted if the user knows the section of the sample to be scanned for calibration. The location would be known if, for example, the user had prepared a set of similar samples and determined the calibration area on a first sample in the set.

The system 10 next sets the gain of the detector 20 and the level of attenuation of the attenuator 16 to a second set of default values (step 406). In the example, the system sets the attenuation level to one-half and the gain of the detector to maximum, which are the same as the first set of default values. The system then uses the laser 12 to re-scan a selected first scan line 301 in the calibration area and produce associated data signals (step 408). If the data signals associated with N adjacent pixels in the scan line 301 are saturated, the system increases the level of attenuation to reduce the excitation signal power by a predetermined factor, in the example, by a factor of two (steps 410, 414). In the example, N is selected between 2 and 8. The system then re-scans the scan line 301, to determine if the signals associated with N adjacent pixels are still saturated (step 410). If so, the system determines if the excitation signal power is at a predetermined minimum, in the example one-quarter of the maximum power. If the power is not at the minimum, the system reduces the signal power by a factor of two by again increasing the attenuation level (steps 412, 414).

If the excitation signal power is at the minimum level and N adjacent pixels in the line still produce saturated signals, the system 10 lowers the gain of the detector 20 by a predetermined factor, in the example by a factor of eight, and also reduces the level of attenuation to increase the laser power by a factor of four (step 416). The system again scans the line 301 and determines if the signals that correspond to N adjacent pixels in the line are saturated. As necessary, the system again automatically and iteratively adjusts the levels of attenuation and gain by the predetermined factors until fewer than N adjacent pixels produce saturated signals (steps 410–416).

The system 10 then skips L lines, in the example L=4, and scans the next, L+1$^{st}$, scan line 306 (steps 420, 408). As necessary, the system automatically adjusts the attenuation and gain levels until the signals associated with fewer than N adjacent pixels in the scan line 306 are saturated. The system then continues to skip L lines, scan a next L+1$^{st}$ scan line and automatically adjust the attenuation and gain levels until the entire calibration area has been scanned in this manner (step 418). The result is a calibrated system and a sample in which a majority of the lines are untouched by the excitation signal.

As discussed, the system preferably performs its calibration operation by rescanning the same scan lines that were scanned to locate the micro-array. During the calibration operation the system 10 may instead scan lines near or adjacent to the lines scanned to locate the micro-array, because of system tolerances for re-tracing the lines. However, even if the same lines are not scanned for both operations, the result is still the same, namely, a calibrated system and a sample in which a majority of the lines are untouched by the excitation signal.

At the end of the low-resolution scanning operation, the system corrects the attenuation level such that the signals produced for the M brightest adjacent pixels in the calibration area have an average value that is 90% of a predetermined maximum data signal value (step 422). The system thus determines the average signal value for the M adjacent brightest pixels, where M is selected between 4 and 32. The system then calculates the level of excitation signal power that is required to produce an average signal value that is 90% of the maximum data signal value for the system. Finally, the system adjusts the attenuation level appropriately.

If the signal power required to produce the desired average value is above the maximum signal power, the system 10 indicates to the user that the fluorescence produced by the micro-array 42 is dim (step 424–425). Otherwise, the system repeats steps 406–424 for the channel associated with the laser 14 (step 426). The system thus "balances the channels."

As discussed above, the system re-scans the selected scan lines a number of times during the calibration operation. Accordingly, the fluorescence produced during the calibration operation may be weaker than the fluorescence that will be produced during a subsequent data collection operation that involves a plurality of previously unscanned lines. The system thus sets the average signal value to 90% of the maximum value, to avoid saturation during the data collection operation. The system may instead set the average value to other percentages, as appropriate.

The method of operation described above with reference to FIG. 4 includes automatically and interactively adjusting the levels of both attenuation and detector gain. The method may also be used in systems that iteratively adjust only one of these levels, by following the steps associated with the adjustment of that level and ignoring the steps associated with adjusting the other level. As discussed also above, the power level of the excitation signal at the sample may be controlled by adjusting a control signal that is supplied to the excitation signal source. The method described above may thus automatically and iteratively adjust the control signal rather than the level of attenuation.

The method described above for automatically adjusting the levels may also be used by systems that scan every line during calibration operations. In such systems this method has the advantages of reliability and repeatability over prior methods that involve user judgment.

Figure 5:
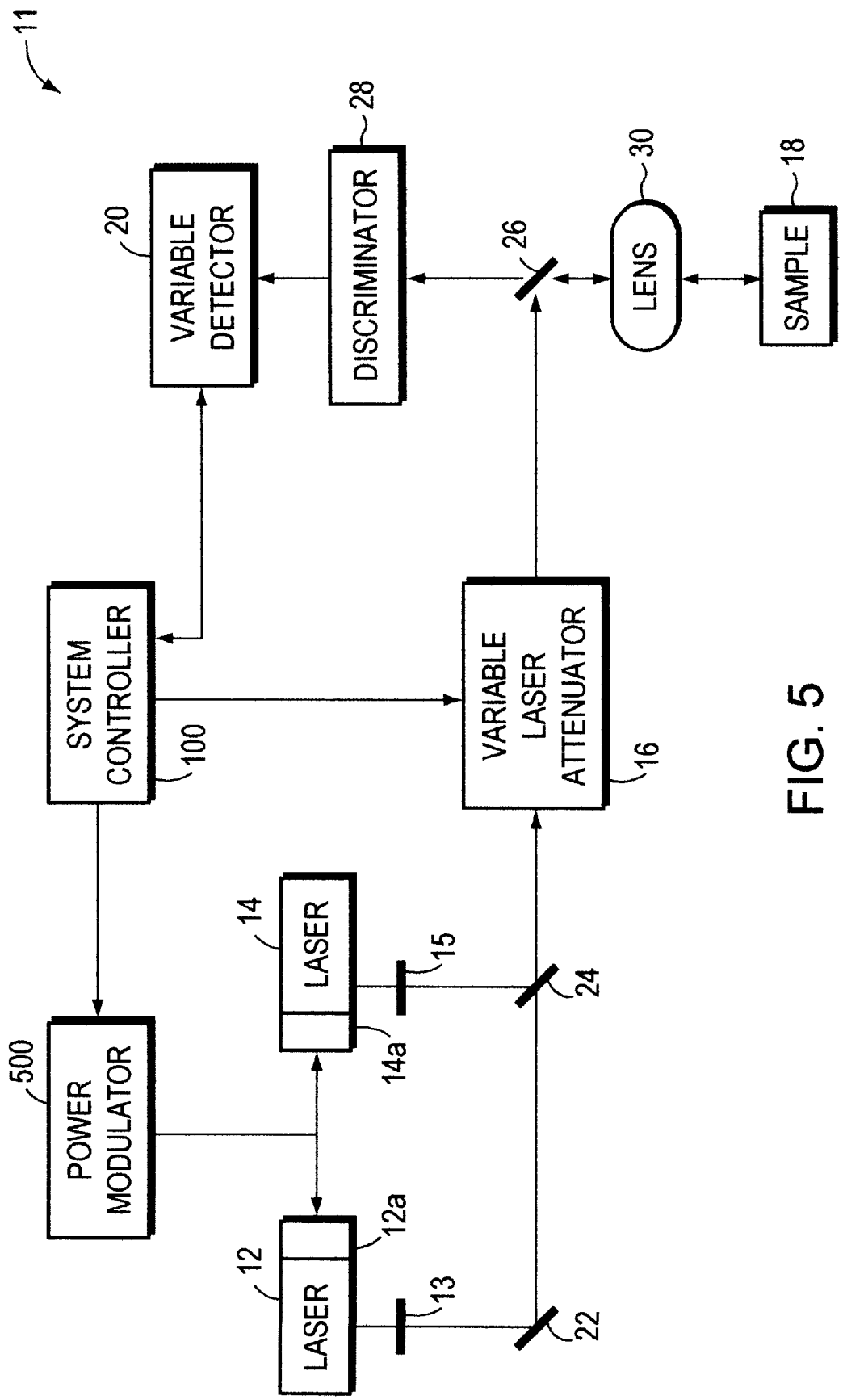
FIG. 5 is a functional block diagram of a system constructed in accordance with a second embodiment of the invention.

Referring now to FIG. 5, a system 11 optionally includes a power modulator 500 that controls laser excitation sources 12a and 14a, to essentially turn the lasers 12 and 14 off for some fraction of the time that the system is scanning across a scan line. The system thus performs low-resolution scanning on a per-scan-line basis, that is, pixel-by-pixel, as well as over the calibration area. Specifically, the system turns off the lasers for a fraction of the scanning of each element, or dot, in the scan line. As discussed, the system need not have determined the locations of the individual elements in the micro-array, as long as the width, or diameters, of the elements are known. The system then turns the lasers 12 and 14 off for times that translate to a fraction of the width of each of the elements.

If the lasers are turned on and off, the system determines if N consecutively acquired pixels are saturated in a given scan line, since N adjacent pixels may not be acquired. Similarly, the system corrects the attenuation based on the M brightest consecutively acquired pixels.

The systems 10 and 11 automatically set the system sensitivity for a given sample. Thus, a user need not manually adjust attenuation and/or gain levels, and the systems are calibrated without relying on the judgment of the user. Accordingly, the systems can be reliably and relatively quickly calibrated. As discussed above, the low-resolution scanning operation leaves untouched the majority of each element of the micro-array for data collection scanning operations. This is in contrast to known prior systems that scan and thus potentially damage every line of a sample, or every line in a portion of the sample, during the calibration operation.

The foregoing description has been limited to a specific embodiment of this invention. It will be apparent, however, that variations and modifications may be made to the invention, such as skipping more or fewer lines during the low resolution scanning operation, setting the attenuation and gain levels to different default values, adjusting the levels by various factors during the low-resolution scanning operation, covering more or less of the image during the low-resolution scanning operation and so forth, with the attainment of some or all of its advantages. Therefore, it is the object of the appended claims to cover all such variations and modifications as come within the true spirit and scope of the invention.

What is claimed is:

1. A method of setting the fluorescence sensitivity of an optical scanning system, the method including the steps of:

A. producing an excitation signal with a predetermined power level;

B. scanning a first scan line of a predetermined calibration area of a sample using the excitation signal;

C. determining if signals corresponding to N pixels in the first scan line are saturated;

D. if the signals are saturated reducing the excitation signal power by a predetermined factor;

E. repeating steps B–D until the signals associated with fewer than N pixels in the first scan line are saturated;

F. scanning a next scan line of the calibration area;

G. determining if signals corresponding to N adjacent pixels in the next scan line are saturated;

H. if the signals are saturated reducing the excitation signal power by the predetermined factor;

I. repeating steps G–H until the signals associated with fewer than N pixels in the next scan line are saturated; and J. repeating steps F–I until a last scan line in the calibration area is scanned.

2. The method of claim 1 wherein the step of scanning a next scan line includes skipping a plurality of lines between scan lines.

3. The method of claim 1 further including the steps of:

K. adjusting detector gain by a predetermined gain factor when the excitation signal power is reduced to a minimum and the signals associated with N pixels are saturated; and L. when the detector gain is adjusted increasing the excitation signal power by a predetermined factor.

4. The method of claim 1 further including the steps of:

K. determining an average signal value for the signals associated with the M brightest pixels in the calibration area;

L. producing an excitation signal that has a power level that will produce for the M brightest pixels associated signals that have a predetermined average signal value.

5. The method of claim 2 wherein the step of skipping a plurality of lines includes skipping a number of lines that produces a spacing between scan lines that is at least twice as wide as the scan line.

6. The method of claim 2 wherein the step of skipping a plurality of lines includes selecting scan lines that are spaced no further than one half of the diameter or width of a sample element.

7. The method of claim 1 further including the step of repeating steps A–J using a next excitation signal.

8. The method of claim 7 further including the step of turning the excitation signal and the next excitation signal off for selected portions of a scan line.

9. The method of claim 3 further including the step of repeating steps A–L using a next excitation signal.

10. The method of claim 9 further including the step of turning the excitation signal and the next excitation signal off for selected portions of a scan line.

11. The method of claim 1 wherein in the step of determining if signals are saturated includes selecting N consecutively acquired pixels.

12. The method of claim 4 wherein the step of determining an average value selects M consecutively acquired pixels.

13. The method of claim 1 further including the step of turning the excitation signal off for selected portions of a scan line.

14. A method of setting the fluorescence sensitivity of an optical scanning system, the method including the steps of:

A. setting detector gain at predetermined maximum level;

B. scanning a first scan line of a predetermined calibration area of a sample using an excitation signal;

C. determining if signals corresponding to N pixels in the first scan line are saturated;

D. if the signals are saturated decreasing the detector gain by a predetermined factor;

E. repeating steps B–D until the signals associated with fewer than N pixels in the first scan line are saturated;

F. scanning a next line of the calibration area;

G. determining if signals corresponding to N pixels in the next scan line are saturated;

H. if the signals are saturated decreasing the detector gain by a predetermined factor;

I. repeating steps G–H until the signals associated with fewer than N pixels in the next scan line are saturated; and repeating steps F–I until a last scan line in the calibration area is scanned.

15. The method of claim 14 further including the steps of:

J. determining an average signal value for the signals associated with the M brightest pixels in the calibration area; and K. adjusting a level of attenuation to produce an excitation signal that will produce for the M brightest pixels associated signals that have a predetermined average value.

16. The method of claim 14 further including, in the step of scanning a next scan line, skipping a plurality of lines between scan lines.

17. The method of claim 16 wherein the step of skipping a plurality of lines includes skipping a number of lines that produces a spacing between scan lines that is at least twice as wide as the scan line.

18. The method of claim 16 wherein the step of skipping a plurality of lines includes selecting scan lines that are spaced no further than one half of the diameter or width of a sample element.

19. The method of claim 14 further including the step of repeating steps A–J using a next excitation signal.

20. The method of claim 19 further including the step of turning the excitation signal and the next excitation signal off for selected portions of a scan line.

21. The method of claim 15 further including the step of repeating steps A–L using a next excitation signal.

22. The method of claim 21 further including the step of turning the excitation signal and the next excitation signal off for selected portions of a scan line.

23. The method of claim 14 wherein in the step of determining if signals are saturated includes selecting N consecutively acquired pixels.

24. The method of claim 15 wherein the step of determining an average value selects M adjacent pixels.

25. A method of setting the fluorescence sensitivity of an optical scanning system, the method including the steps of:

A. producing an excitation signal at a predetermined power level and setting detector gain at predetermined maximum level;

B. scanning a first scan line of a predetermined calibration area of a sample using the excitation signal;

C. determining if signals corresponding to N pixels in the first scan line are saturated;

D. if the signals are saturated and the excitation signal power is not at a predetermined minimum, reducing the excitation signal power by a predetermined factor;

E. if the signals are saturated and the excitation signal power is at a predetermined minimum, decreasing a detector gain by a predetermined factor and increasing the excitation signal power by a predetermined factor;

F. repeating steps B–E until the signals associated with fewer than N pixels in the first scan line are saturated;

G. skipping a plurality of lines and scanning a next line of the calibration area;

H. determining if signals corresponding to N pixels in the next scan line are saturated;

I. if the signals are saturated and the excitation signal power is not at a predetermined minimum, reducing the excitation signal power by a predetermined factor;

J. if the signals are saturated and the excitation signal power is at a predetermined minimum, decreasing the detector gain by a predetermined factor and increasing the excitation signal power by a predetermined factor;

K. repeating steps H–J until the signals associated with fewer than N pixels in the next scan line are saturated; and L. repeating steps G–K until a last scan line in the calibration area is scanned.

26. The method of claim 25 further including the steps of:

M. determining an average signal value for the signals associated with the M brightest pixels in the calibration area; and N. producing an excitation signal has a power level that will produce for the M brightest adjacent pixels associated signals that have a predetermined average value.

27. The method of claim 25 wherein the step of skipping a plurality of lines includes skipping a number of lines that produces a spacing between scan lines that is at least twice as wide as the scan line.

28. The method of claim 25 wherein the step of skipping a plurality of lines includes selecting scan lines that are spaced no further than one half of the diameter or width of a sample element.

29. The method of claim 25 further including the step of repeating steps A–L using a next excitation signal.

30. The method of claim 26 further including the step of repeating steps A–N using a next excitation signal.

31. The method of claim 25 further including turning the excitation signal off for selected portions of a scan line.

32. The method of claim 29 further including the step of turning the excitation signal and the next excitation signal off for selected portions of a scan line.

33. The method of claim 30 further including the step of turning the excitation signal and the next excitation signal off for selected portions of a scan line.

34. The method of claim 25 wherein in the step of determining if signals are saturated includes selecting N consecutively acquired pixels.

35. The method of claim 26 wherein the step of determining an average value selects M consecutively acquired pixels.

* * * * *